United States Patent [19]

Marmar

[11] Patent Number: 4,865,590
[45] Date of Patent: Sep. 12, 1989

[54] DISPOSABLE PROSTATIC ASPIRATION DEVICE

[76] Inventor: Joel L. Marmar, 1301 N. Kings Hwy., Cherry Hill, N.J. 08034

[21] Appl. No.: 95,051

[22] Filed: Sep. 9, 1987

[51] Int. Cl.$^4$ ............................................. A61M 5/32
[52] U.S. Cl. .................................. 604/180; 604/263; 128/329 R
[58] Field of Search ............... 604/180, 192, 158, 263, 604/754, 93, 265, 750, 198; 128/DIG. 26, 304, 303 R, 329, 361

[56] References Cited

U.S. PATENT DOCUMENTS

| | | | |
|---|---|---|---|
| 2,486,056 | 10/1949 | Oclassen | 604/192 |
| 2,811,969 | 11/1957 | Shubert | 128/303 R |
| 3,046,984 | 7/1962 | Eby | 604/180 |
| 3,741,211 | 6/1973 | Vreeland, Jr. | 128/329 |
| 3,826,254 | 7/1974 | Mellor | 604/180 |
| 3,854,483 | 12/1974 | Powers | 604/172 |
| 4,057,066 | 6/1977 | Taylor | 604/180 |
| 4,170,993 | 10/1979 | Alvarez | 604/263 |
| 4,269,310 | 5/1981 | Uson | 604/172 |
| 4,457,754 | 7/1984 | Buttaravoli | 128/DIG. 26 |
| 4,460,356 | 7/1984 | Moseley | 604/180 |
| 4,555,243 | 11/1985 | Markham | 128/329 R |
| 4,583,976 | 4/1986 | Ferguson | 128/DIG. 26 |

FOREIGN PATENT DOCUMENTS

86/06641  11/1986  PCT Int'l Appl. ......... 128/DIG. 26

*Primary Examiner*—John D. Yasko
*Attorney, Agent, or Firm*—Ratner & Prestia

[57] ABSTRACT

A disposable aspiration needle guide comprising a plastic guide channel or tube through which an aspiration needle may be passed attached to a planar flexible support having an adhesive coating on one surface thereof. The needle guide is adhesively attached along the length of the top or bottom of a physician's gloved finger. A pharmaceutically acceptable preparation of an antibiotic compound can be deposited in the interior of the tube to deliver a high concentration of antibiotic to a puncture site when an aspiration needle is inserted therethrough.

14 Claims, 1 Drawing Sheet

DISPOSABLE PROSTATIC ASPIRATION DEVICE

FIELD OF THE INVENTION

This invention relates generally to medical devices and, more specifically, to a disposable guide for needle aspiration of the prostate gland. Preferred forms of the invention include a thin flexible channel, or tube, centrally mounted along the length of a flexible support adapted for attachment along the length of a gloved finger and taped securely to the finger and distal palm of the hand.

BACKGROUND OF THE INVENTION

During the course of a physical examination on adult males, it is common to perform a rectal examination and palpate the prostate gland. In its healthy state, the prostate gland feels soft and spongy. In cases of possible neoplasm, the gland may feel hard and present as a nodule. Whenever a hard nodule is detected, it must be biopsied in order to obtain tissue for pathologic confirmation of the diagnosis.

Prostatic biopsies have been performed by inserting a needle into the gland to sample tissue. The examiner may use a large #14 gauge biopsy needle to obtain a core of tissue (1×3 mm) which is processed for histologic interpretation, or he may use a thin #22 gauge needle to obtain exfoliated cells by aspiration for cytologic interpretation.

If the larger #14 gauge needle is used, ample tissue is generally obtained, but there is a greater risk of bleeding and sepsis because of the relatively large puncture site. Often, repeat biopsies may be required when the core sample is negative for cancer. These repeat biopsies increase the risk of possible complications.

In contrast, if the thin #22 gauge needles are used, then the likelihood of bleeding and sepsis are significantly reduced. The puncture site is small and these needles produce minimal tissue trauma. The prostatic epithelium may be exfoliated from a diffused fan-shaped area in and around the nodule as the needle is withdrawn and reinserted into the gland several times. Recent literature (J. Urology, Vol. 113:955, 1986), suggests that these aspiration techniques increase accuracy over the single core biopsy, and may reduce the risk of complications.

These biopsies may be performed either by the transperineal or transrectal route. However, in order to accurately position the needle through the perineum, expensive ultrasound equipment may be required. In contrast, accurate transrectal placement may be accomplished by means of a simple finger guide. Presently, the transrectal prostatic aspiration biopsy with a finger guide has been widely accepted in clinical practice (J. Urology, Vol. 135:294, 1986). These procedures may be performed inexpensively, in an office setting, even without local anesthesia.

In an attempt to facilitate a low cost and reliable transrectal prostatic aspiration biopsy, I have invented a new disposable flexible needle guide. In the following paragraphs, the prior art will be discussed and the new invention will be compared to these older devices.

U.S. Pat. No. 3,595,217 describes a needle aspiration guide. The '217 patent discloses a needle guide comprising a tubular member or channel having a ring member secured to one end and a stabilizing disk slidably mounted along the length of the channel. In use, one end of the guide is fixed to the operator's gloved index finger by the ring. The disk, positioned in the palm of the operator, facilitates handling of the guide and maintains stability of the channel. The index finger is inserted into the rectum of the patient, and the prostate is palpated. When a suspicious nodule is palpated, a needle is passed through the tubular member in order to puncture and aspirate the suspicious area.

Although this needle guide is durable, it has a number of disadvantages. First, it must be sterilized between cases, which may take time and risks cross-contamination between patients. Additionally, the ring member, attached to the finger of the examiner, may be uncomfortable to the patient as it passes through the anal sphincter. Furthermore, the ring member may also be uncomfortable to the examiner when placed over the tip of the index finger. Also, the hard construction of the ring can interfere with palpation which may make accurate diagnosis difficult.

In the medical publication, "The Lancet," Sept. 1, 1984, page 495, a needle guide is described for use with a #14 gauge needle. This guide comprises a generally flexible collar or ring mounted on the carrier portion through which a gloved index finger may be inserted. Mounted on the base of the carrier portion is a flexible sheath through which a needle may be inserted. Disposed between the flexible sheath and the carrier portion is a stiffener to facilitate insertion of the needle. In use, the finger is inserted into the collar portion so that the volar aspect of the finger is in contact with the carrier. The finger and carrier are then inserted into the rectum of the patient, and the prostate gland or nodule is palpated in the usual manner.

While this needle guide offers some improvements over the one disclosed in the '217 patent, it also has a number of disadvantages. The guide is designed for a large size #14 gauge needle. Furthermore, the carrier portion supporting the flexible sheath, stiffener, and collar may be uncomfortable to the patent as it passes through the anal sphincter. Furthermore, the stiffener placed between the flexible sheath and the carrier portion may make accurate palpation difficult. Still further, this needle guide does not provide adequate stabilization because the collar surrounds only a small circumference of the index finger (around the second joint). Also, since this device is worn over the tip of the index finger, it may inhibit natural movement of the finger as digital examination is being performed. Although this guide is intended to be disposable, it still embodies all of the disadvantages mentioned above.

DESCRIPTION OF THE INVENTION

A disposable aspiration needle guide, constructed in accordance with the present invention, includes a flexible channel or tube through which an aspiration needle may be passed. The tube is attached to a planar flexible support having an adhesive coating on one surface thereof. The support, with the tube attached, is adhesively secured along the length of the top or bottom of the physician's gloved finger. In use, the finger is inserted into a patient's rectum for a digital examination. When a suspicious nodule is palpated, a needle is passed through the tube to puncture and aspirate the suspicious area.

Another feature of the invention includes a tube loaded in its interior with a pharmaceutically acceptable preparation of an antibiotic compound, such as Betadine. The insertion of the needle pushes the antibiotic forward as the needle passes through the tube. This delivers a high concentration of the antibiotic to the rectal mucosa at the puncture site.

DETAILED DESCRIPTION OF THE INVENTION

Figure 1:
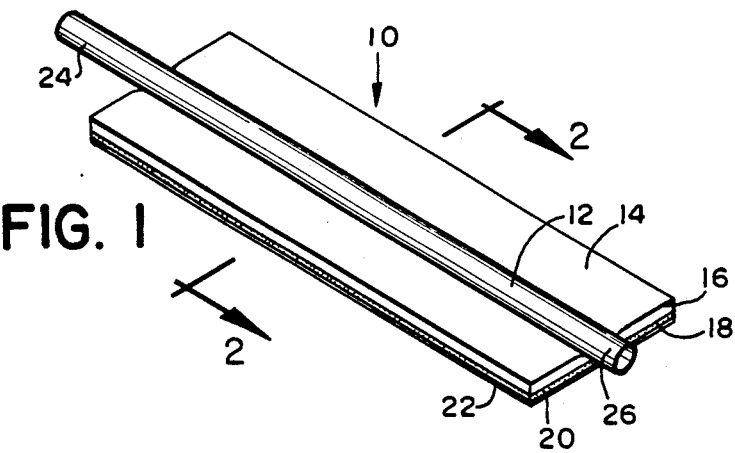
FIG. 1 is a top perspective view of a needle guide constructed in accordance with the present invention.
Figure 2:
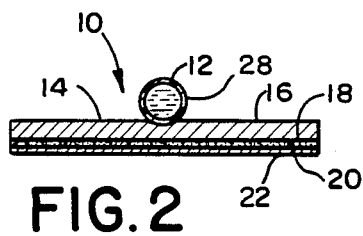
FIG. 2 is an enlarged, detailed, cross-sectional view taken along line 2—2 in FIG. 1.

Referring to FIGS. 1 and 2, there is shown a needle guide 10 of the present invention. Guide 10 includes a flexible plastic channel or tube 12 attached to a planar flexible support 14 centrally along the longitudinal axis of the support. Flexible support 14 has a first surface 16 and a second surface 18. The second surface has an adhesive coating 20 for adhesively securing the needle guide to a gloved finger. Support 14 may be, for example, a strip of adhesive tape. Preferably, support 14 is of sufficient length (typically from 50 to 100 millimeters) to permit attachment along a substantial length of the gloved finger. A non-porous, paper-thin removable cover 22 of the same shape and size as the flexible support is placed over the adhesive coating to protect the adhesive coated surface until the needle guide is ready for use.

Figure 4:
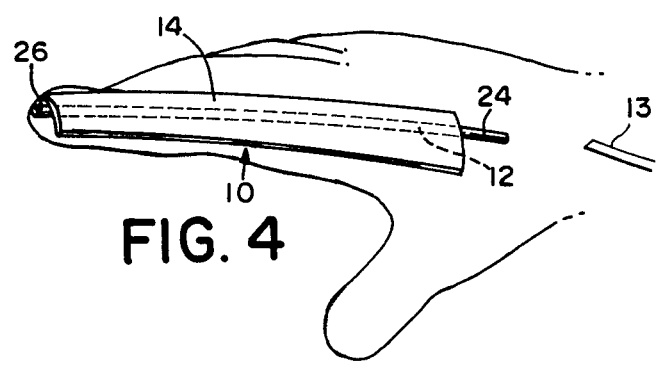
FIG. 4 shows a needle guide, constructed in accordance with the present invention, attached in place on the upper surface of a gloved finger.

As can be seen from the illustrated embodiment, tube 12, through which an aspiration needle 13, shown in part in FIG. 4, may be passed, is of a length greater than that of support 14 and includes needle receiving end 24 extending substantially beyond one end of the support and a needle exiting end 26 extending only several millimeters beyond the opposite end of the support. Typically, tube 12 is from 60 to 175 millimeters in length.

Tube 12 may be attached to support 14 by a number of known methods, such as by ultrasonic or heat welding, or by an adhesive, or by any other suitable means. Although in the FIG. 1 embodiment of the invention, tube 12 is attached to surface 16, the tube may be attached to surface 18 or attached to adhesive coating 20, as shown in FIGS. 3 and 4.

Figure 3:
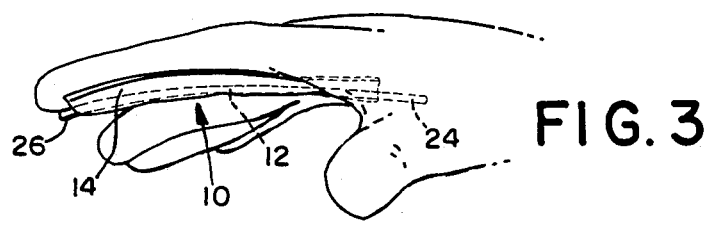
FIG. 3 shows a needle guide, constructed in accordance with the present invention, attached in place on the bottom of a gloved finger.

FIG. 3 shows a needle guide of the present invention adhesively attached to the underside of a gloved finger. In use, the needle guide 10, after having cover 22 removed, is adhesively mounted so that the lower plane of the gloved finger is in contact with the adhesive coated surface 20 of support 14 and the terminal phalanx of the gloved finger is protruding several millimeters beyond the end of the support.

FIG. 4 shows an alternative placement of needle guide 10 on the upper surface of the gloved finger, thereby exposing the lower aspect of the gloved finger so that the lower portion of the gloved finger remains virtually unobstructed.

As previously mentioned, complications such as bleeding and/or sepsis can result from prostate biopsies, particularly when the trans-rectal method is used. While the use of thin gauge needles has lessened the likelihood of such complications, they ar not entirely eliminated. A particular feature of an embodiment of the present invention is an antibiotic compound or ointment 28, shown in FIG. 2, deposited in the interior of the tube. The antibiotic is delivered to the site of the puncture when the aspiration needle is inserted therethrough. The presence of such compounds reduces the likelihood of infection which is associated with trans-rectal punctures.

In general, support 14 is of a length suitable to facilitate mounting along the length of one side of a gloved finger, with tube 12 extending beyond both ends of support 14. Mounting the needle guide in this manner serves to stabilize the needle guide along its length when in use. Positioning one end of support 14 at the tip of the gloved finger, facilitates accurate placement of an aspiration needle by permitting the distal portion of the gloved finger to palpate the prostate (and/or nodule) without any obstruction or interference. Furthermore, since needle receiving end 24 extends substantially beyond the end of support 14, an aspiration needle may conveniently be inserted in needle receiving end 24, while located outside of the body of a patient, after the needle guide has been inserted into the patient's rectum.

While this invention has been described with reference to specific, particularly, preferred embodiments thereof, it is not limited thereto and the appended claims are intended to be construed to embody not only the specific forms and variants of this invention shown, but to such other forms and variants as may be devised by those skilled in the art without departing from the true spirit and scope of this invention.

What is claimed:

1. An aspiration needle guide adapted for attachment along the length of a finger, said guide comprising:
    a planar flexible support having a width sized to extend over a selected circumferential extent of a finger and a length substantially greater than its width and sized to extend along a substantial length of a finger;
    an adhesive coating on a planar surface of said support;
    and a thin, flexible tube permanently attached to said support and extending along the length of said support beyond the ends of said support.

2. A needle guide as recited in claim 1 further including a releasable cover adhered to said adhesive coating of said support.

3. A needle guide as recited in claim 2 where one end of said tube extends beyond one end of said support further than the opposite end of said tube extends beyond the opposite end of said support.

4. A needle guide as recited in claim 3 wherein said tube is attached on said planar surface.

5. A needle guide as recited in claim 3 wherein said tube is attached to the planar surface of said support opposite from said planar surface having said adhesive coating.

6. A needle guide as recited in claim 1 wherein said tube is from 60 millimeters to 175 millimeters in length.

7. A needle guide as recited in claim 1 wherein said tube is about 150 millimeters in length.

8. A needle guide as recited in claim 1 further including, in the interior of said tube, a pharmaceutically acceptable preparation of an antibiotic compound.

9. A needle guide as recited in claim 1 wherein said flexible tube is plastic.

10. A needle guide as recited in claim 9 further including, in the interior of said tube, a pharmaceutically acceptable preparation of an antibiotic compound.

11. An aspiration needle and guide assembly comprising:

an aspiration needle guide adapted for attachment along the length of a finger and comprising a planar flexible support, an adhesive coating on a planar surface of said support, and a thin, flexible, tube permanently attached to said support and extending longitudinally beyond the ends of said support; and an aspiration needle inserted within said flexible tube.

12. An aspiration needle and guide assembly according to claim 11 further including, in the interior of said tube, a pharmaceutically acceptable preparation of an antibiotic compound.

13. An aspiration needle and guide assembly comprising:

an aspiration needle guide adapted for attachment along the length of a finger, said guide including:
  (i) a planar flexible support having a width sized to extend over a selected circumferential extent of a finger and a length substantially greater than its width and sized to extend along a substantial length of a finger,
  (ii) an adhesive coating on a planar surface of said support, and
  (iii) a thin, flexible tube permanently attached to said support and extending along the length of said support beyond the ends of said support;
and an aspiration needle inserted within said flexible tube.

14. An aspiration needle and guide assembly according to claim 13 further including, in the interior of said tube, a pharmaceutically acceptable preparation of an antibiotic compound.

* * * * *